United States Patent [19]

Nevo et al.

[11] Patent Number: 4,642,120
[45] Date of Patent: Feb. 10, 1987

[54] REPAIR OF CARTILAGE AND BONES

[75] Inventors: Zvi Nevo, Herzlia; Samuel Itay, Kfar Saba, both of Israel

[73] Assignee: Ramot University Authority for Applied Research and Industrial Development Ltd., Tel-Aviv, Israel

[21] Appl. No.: 591,822

[22] Filed: Mar. 21, 1984

[30] Foreign Application Priority Data

Mar. 23, 1983 [IL] Israel .......................................... 68218

[51] Int. Cl.$^4$ ............................ A61F 2/28; A61F 2/02
[52] U.S. Cl. ......................................... 623/16; 623/11; 623/66; 623/15; 128/92 R; 128/92 W; 128/156; 128/92 YG; 128/92 YR; 128/92 YQ; 424/95; 435/244; 435/245
[58] Field of Search ....................... 623/11, 15, 16, 66; 128/92 C, 92 R, 92 G, 155, 156; 424/108, 109, 95; 435/244, 243

[56] References Cited

FOREIGN PATENT DOCUMENTS 36545 3/1983 Japan ...................................... 623/66

OTHER PUBLICATIONS

"Bone Cell Differentiation and Growth Factors"; Urist et al., *Science* (Washington, DC), 1983, 220 (4598), 680–6.

Primary Examiner—Richard J. Apley
Assistant Examiner—Gregory Beaucage
Attorney, Agent, or Firm—Fleit, Jacobson, Cohn & Price

[57] ABSTRACT

There are provided compositions for repairing defects of cartilage and bones. These are provided in gel form either as such, or embedded in natural or artificial bones. The gel comprises certain types of cells. These may be committed embryonal chondocytes or any kind of mesenchyme originated cells which potentially can be converted to cartilage cells, generally by the influence of chondrogenic inducing factors, in combination with fibrinogen, antiprotease and thrombin. The cells ought to be of the species to which the composition is transplanted. It is advantageous to incorporate in the gel extracellular matrix (ECM) of chondrocytes or other hormones and/or growth factors such as SM (Somatomedin=IGF−I), FGF (fibroblast growth factor), CGF (cartilage growth factor), BDGF (bone derived growth factor) or a combination of any of these.

8 Claims, No Drawings

REPAIR OF CARTILAGE AND BONES

FIELD OF THE INVENTION

There are provided compositions for use in the repair of defects of articular cartilage and defects of bones by transplantation. The compositions of the invention can be used for such repairs. They are provided in the form of gels, either as such, or in combination with natural or artificial bones as carrier. The following description relates mainly to repairs of articular cartilage as this is one of the most problematic and delicate biological structures. The novel compositions comprise in combination, embryonal chondrocytes or certain mesenchyme cells which potentially can be converted to cartilage cells by the influence of chondrogenic inducing factors, the cells being combined with suitable quantities of fibrinogen, thrombin and antiprotease serving as a glue. The resulting gels can be stored during prolonged periods of time under tissue culture storage conditions, and can be transported and handled with ease.

According to a preferred embodiment of the invention extracellular matrix (ECM), or certain growth factors such as SM, FGF, CGF, BDGF or a combination of any of these, can be incorporated in such gels. For the repair of certain defects of bones there may be used implants comprising suitably shaped bone members imbued with such gels.

Other and further features of the invention will become apparent hereinafter.

BACKGROUND OF THE INVENTION

When articular cartilage is damaged by trauma, infection or degenerative processes, such damages generally fail to heal or even improve. Hitherto various attempts have been made to resort to osteochondral grafts and to the provision of various forms of prosthesis, but long term results have been poor and discouraging. There have been reported attempts to use cultured chondrocytes as a source of cartilage transplants, but integration of the transplants with the neighboring cartilage was generally unsatisfactory.

SUMMARY OF THE INVENTION

According to the invention there are provided readily usable compositions comprising cells, such as embryonal chondrocytes or any kind of mesenchyme originated cells which can be converted in vitro or in vivo, to cartilage cells by the influence of chondrogenic inducing factors, in a suitable biological milieu, which forms a "gel" which can be used for the repair of damages to adult articular cartilage and bone by transplantation to the site of the damage. There is also provided a process for the production of such implantable material.

There is also provided a composition for use in the repair of defects of cartilage. The compositions are prepared by the isolation of embryonal chondrocytes (young commited chondrocytes) by trypsinization with mechanical disintegration of the suitable embryonal tissue, followed by cultivation on a suitable medium, harvesting the cells, admixing them with fibrinogen, antiprotease and thrombin, to result in a gel, which can be stored for limited periods of time in an incubator, or which the harvested cells can be preserved for prolonged periods of time by deep freezing and thawing before use to the desired gel. The gel is immersed in a solution of fibrinogen before application to the site of implantation which has been sprayed with a thrombin solution, to fill up the defect. It has been shown in animal experiments (with avian and mammalian species) that defects of cartilage and bone are filled up properly, as inspected after periods of 2 to 12 months, showing excellent repairs of the initial damage.

The compositions of the invention are of value in repairing damages of human articular cartilage or bone due to trauma or old age. Such damages in various types of cartilage and bone, including degenerative injuries and fractures of joints.

According to a preferred embodiment of the invention, the novel preparation of the invention includes a certain quantity of extracellular matrix (ECM) of embryonal chondrocytes, which is prepared by a specific technique, as set out in the following.

The provision of the ECM enhances the growth of the chondrocytes when the novel composition is implanted, most probably as these resemble the desired natural environment.

The chondrocytes are obtained from a suitable embyronal epiphyseal tissue of the species to which the transplanted material is to be applied. Allogeneic cells give entirely satisfactory results without the necessity to resort to HLA typing. For use in humans, human embryonal chondrocytes were cultivated.

It has been found that the number of chondrocytes per unit volume ought not to exceed a certain value, as otherwise necrosis of the cells occurs and inferior results are obtained. Representative values of chondrocyte concentrations are about 100,000 to 500,000 per milliliter of the gel. There are used about 5 to 50 units thrombin per milliliter and about 25 to 80 mg/ml fibrinogen. Generally protease inhibitor is added to the composition to prevent or repress fast lysis of the gel. There may be used natural or synthetic protease inhibitors. Suitable protease inhibitors are chemical inhibitors such as $\epsilon$-aminocaproic acid, used in quantities of about 10 to 20 mg/ml of gel; tranexemic acid, used in quantities of about 1 to 2 mg/ml of gel. There may be used a natural protease inhibitor such as anti-trypsin (Chicken-eggwhite, Sigma, Type III) in concentrations of 50–75 $\mu$g/ml. When a slow formation of the gel is desired, a quantity of the order of 5 to 10 units/ml thrombin is used when a quick setting of the gel is desired, quantities of the order of 20 to 50 units/ml thrombin are used.

In addition to the above, it is advantageous to incorporate in the gel one or more growth factors of the local type (e.g. ECM, BDGF) or of the hormonal type, e.g. Somatomedin (SM)-like peptides; cartilage growth factor (CGF); and the like. Growth factors are used in the following orders of magnitude: ECM: some mg/ml; BDGF: in the order of 100 microgram/ml; CGF: a few nanograms/ml; SM: a few nanograms/ml.

The compositions covered with F-12 plus 10% fetal calf serum, can be stored in a $CO_2$ incubator for a few weeks, at about 37° C. The gels according to the invention are ready for use, and can be applied directly to the injured or defective site, as will be set out in the following.

For certain repairs it is feasible to utilize implants which consist of a bone structure (natural or artificial) imbued with a gel consisting of thrombin, antiprotease, fibrinogen and one or more growth factors and/or hormones with a small concentration of the type of cells defined above, or even without such cells. In the latter case, the cells from the environment slowly penetrate into the implant and form a coherent entity between surroundings and implant.

DESCRIPTION OF THE PREFERRED EMBODIMENT

The invention is illustrated with reference to the following example, which is to be construed in a non-limitative manner.

EXAMPLE 1

Preparation of Composition for Cartilage Repair

As starting material there were used epiphyses of long bones (tibia, femur).

The isolation procedure of embryonal chondrocytes (young committed chondrocytes) comprises a drastic trypsinization of the epiphyses (1% trypsin incubated for 45 min. on a rotatory shaker in a water bath at 37° C., simultaneously with a constant mechanical disintegration of the tissue by a hand channeled-Teflon homogenizer). Trypsin activity is terminated by serum which contains antiproteolytic substances. The resulted single cell suspension is seeded then for several days (6–10 days) in liquid Ham F-12 medium on plates coated with soft agar (0.6% agar, containing Ham-F-12). During this growth period most of the fibroblasts are dying off and chondrocyte enrichment does occur. The cells from the soft agar plates are further transferred to grow in suspension cultures of F-12 in Spinner bottles, for an additional period of 3–10 days. The growth conditions in Spinner bottles again support preferentially chondrocytes over fibroblasts. The cells from the Spinner bottles are collected by centrifugation and used directly or cryopreserved (20% Fetal Calf serum, 10% Dimethyl sulfoxide (DMSO) and 70% F-12) in liquid nitrogen for longer periods. The resulting pellet of chondrocytes is resuspended in a small volume of phosphate buffer saline containing fibrinogen (50 mg/ml) or any other serum clotting protein and a trypsin-inhibitor (50 µ/ml, Sigma Type III) or any other antiprotease.

The latest solution containing cells (ranging in concentration between $1-5 \times 10^5$ cells/ml depending on age in culture and size), fibrinogen and trypsin-inhibitor is designated as solution A. To a microtest plate (96 F Nunc Denmark with lid) or multiple wells, 30 microliter of thrombin solution (Solution B) (1U/30 ml of 40 mM $CaCl_2$) is added to each well (distributed evenly on the bottom and on the side walls), then 90 microliters of solution A is added and the mixture is allowed to solidify (gelify).

Depending on the needs, the final quantity can be changed, thus keeping the ratio of solutions A and B 3:1 (v/v). The gels covered with 0.2 ml of F-12 can then be kept for a period of time (about 14 days) in incubator equilibrated with 5–10% $CO_2$ in air, or cryopreserved.

At transplantation, the injured site is sprayed delicately with a thrombin solution, while the gels prior to transplantation are immersed in a solution containing fibrinogen and trypsin-inhibitor (50 mg/ml and 50 ug/ml respectively), and the sample is pressed into the injured site, filling up smoothly the defect.

Instead of embryonal chondrocytes there may be used embryonal mesenchyme cells (stage 24) or bone marrow stem cells. In addition there may be used any adult connective tissue with trapped undifferentiated mesenchyme cells, generating cells in culture which are finally transformed into chondrocytes by self differentiation or directed by chondrogenic factors.

For syngeneic transplants there may be used homogeneic mesenchyme type cells trapped in adult tissues of the recipient, such as skin fibroblasts, bone marrow cells obtained by biopsy, which generate cells in culture, which are converted into chondrocytes.

EXAMPLE 2

Gel Containing ECM (Extracellular Matrix)

a. Preparation of ECM

Embryonal chick chondrocytes from Spinner bottles (14–21 days in culture) were plated at an initial density of $2 \times 10^5$ cells/35 mm dish and maintained in F-12 medium supplemented with ascorbic acid (50 µg/ml) on fibronectin coated dishes. The cultures became confluent within 6 days, the media were then renewed and the cultures were further incubated for additional 6 days. A set of triplicate cultures was trypsisized and used for examining cell counts by a Coulter Counter (Model Industrial D). Cell counts at termination ranged aroung $1 \times 10^6$ cell/plate. All the other plates were then washed with phosphate-buffered saline (PBS), exposed for 20 min. to 20 mM $NH_4OH$ in distilled water, and rewashed 3 times with PBS and the two last washes with distilled water so that no cytoskeletons or nuclei could be observed associated with the intact ECM which coated the dish. The ECM was collected with a rubber policeman and lyophylized. The yields of dry powdered ECM ranged between 0.3–1.0 mg/plate.

The ECM was admixed in quantities of from 5 to 20 mg per ml. Best results were obtained with about 10 mg/ml.

Data collected in experimentation with chondrocyte gels as transplants in several species (avian and mammalian) by macroscopic observation histological sections, and bio-chemical tests showed that at the site of transplantation, within 2–3 months, the defect is filled properly (adjusted to the surroundings, including the surface of the articular cartilage) with active proliferating cartilage cells, expressing characteristic (phenotypic) metabolic traits, and integrated well (with no fibro-cartilage or other soft tissue at the edges), with the old neighboring cartilage tissue.

We claim:

1. A composition of the repair of defects of articular cartilage and bones by implantation, comprising:
   cells selected from the group consisting of embryonal chondrocytes, and mesenchyme cells of the species to which the composition is to be implanted capable of being converted by chondrogenic inducing factors to cartilage cells, and
   a biological glue consisting of fibrinogen, thrombin and a protease inhibitor.

2. The composition according to claim 1, containing from 100,000 to 500,000 chondrocytes or mesenchyme cells per milliliter.

3. The composition according to claim 1, wherein the chondrocytes comprise from 5 to 20 mg/ml extracellular matrix (ECM).

4. The composition according to claim 1, further comprising a local growth factor or a hormonal-growth factor.

5. The composition according to claim 4, wherein the local growth factor is cartilage derived growth factor (CDF) or bone derived growth factor (BDGF).

6. The composition according to claim 4, wherein the hormonal growth factor is somatomedin selected from the group consisting of serum and pituitary somatomedin.

7. The composition according to claim 1, wherein the cells are chondrocytes or cells derived from connective tissue containing undifferentiated mesenchyme trapped, cells which are capable of being induced in culture to proliferate and be converted into chondrocytes.

8. The composition of claim 1 wherein the protease inhibitor is a natural protease inhibitor.

* * * * *